United States Patent [19]

McDaniel et al.

[11] Patent Number: 4,780,897

[45] Date of Patent: Oct. 25, 1988

[54] DUAL ENERGY IMAGING WITH KINESTATIC CHARGE DETECTOR

[75] Inventors: David L. McDaniel, Dousman; Paul R. Granfors, Milwaukee; Gary S. Keyes, Hartland, all of Wis.

[73] Assignee: General Electric Company, Milwaukee, Wis.

[21] Appl. No.: 860,329

[22] Filed: May 6, 1986

[51] Int. Cl.⁴ ............................................ G01N 23/04
[52] U.S. Cl. .......................................... 378/62; 378/5; 378/19; 378/160; 250/385.1
[58] Field of Search ............... 378/5, 19, 99, 114, 378/115, 146, 147, 157, 160, 62; 358/111; 250/385.1

[56] References Cited

U.S. PATENT DOCUMENTS

| | | | |
|---|---|---|---|
| 3,924,133 | 12/1975 | Reiss | 378/114 |
| 4,149,081 | 4/1979 | Seppi | 378/99 |
| 4,190,773 | 2/1980 | Braden et al. | 378/160 |
| 4,193,001 | 3/1980 | Liebetruth et al. | 378/19 |
| 4,255,664 | 3/1981 | Rutt et al. | 378/5 |
| 4,315,157 | 2/1982 | Barnes | 378/19 |
| 4,361,901 | 11/1982 | Daniels et al. | 378/110 |
| 4,399,550 | 8/1983 | Hanok et al. | 378/5 |
| 4,511,799 | 4/1985 | Bjorkholm | 378/5 |
| 4,541,106 | 9/1985 | Belanger et al. | 358/111 |
| 4,626,688 | 12/1986 | Barnes | 250/367 |
| 4,686,695 | 8/1987 | Macovski | 378/99 |
| 4,707,608 | 11/1987 | DiBianca | 250/385.1 |

FOREIGN PATENT DOCUMENTS 0002777 1/1977 Japan ........................ 250/370 E

OTHER PUBLICATIONS

"Kinestatic Charge Detection", by DiBianca et al., Med. Phys. 12(3), May/Jun. 1985, p. 339.

Primary Examiner—Craig E. Church
Assistant Examiner—John C. Freeman
Attorney, Agent, or Firm—James H. Beusse; Douglas E. Stoner

[57] ABSTRACT

A method and apparatus for providing dual energy radiation images of a patient in a kinestatic charge detection system utilizes first and second kinestatic charge detectors commonly connected to apparatus for rotating the detectors about a radiation source at a predetermined velocity. The detectors are adjusted such that ion drift velocity in each detector is equal in magnitude but opposite in direction to the velocity of rotation of the detectors. The radiation from the radiation source is modulated such that relatively low average energy radiation impinging on the patient is received by the first detector and relatively high average energy radiation impinging on the patient is received by the second detector. As the radiation is scanned across the patient and received by the detectors, output data from each detector provides information representative of the intensity of radiation received during the scan. The output data is then combined by a imaging system to form a difference image.

5 Claims, 3 Drawing Sheets

DUAL ENERGY IMAGING WITH KINESTATIC CHARGE DETECTOR

This invention relates to ionization chamber x-ray detectors and, more specifically, to a method and apparatus for obtaining a dual energy difference image in a kinestatic charge detector system.

BACKGROUND OF THE INVENTION

The optimal detection of ionizing radiation in two dimensions is the central problem in computed tomography, digital radiography, nuclear medicine imaging and related disciplines. Many different types of detectors (e.g., non-electronic, analog electronic and digital electronic detectors) have been used with varying degrees of success in these fields. In general, many compromises have been made in the various imaging and non-imaging parameters of detectors in developing operational systems.

More recently, there has been developed a different type of detector known as the kinestatic charge detector (KCD). In a KCD system, there is provided an x-ray detection volume and a signal collection volume formed in a closed chamber. In the detection volume, there is generally disposed some type of medium which will interact with x-ray radiation to produce secondary energy. The medium is generally enclosed within a defined space and the collection volume is preferably a multi-element detector of secondary energy located at one boundary of the detection volume. An applied electric field across the detection volume imparts a constant drift velocity to secondary energy particles or charges driving the charges of one sign towards the signal collection volume. Charges of the other sign will drift in a direction away from the collection volume and will not contribute to any output signal.

In the operation of the system, an x-ray beam scans a patient and the x-ray radiation passing through the patient is directed into the detection volume. The KCD is oriented such that the one-dimensional array of collector electrodes spans the fan beam which is transverse to the direction of scan, and the width of the x-ray beam in the scan direction is matched to the height of the detection volume. The x-ray radiation collides with particles in the medium of the detection volume creating a secondary energy. The electric field across the detection volume is produced between a first electrode at one side of the detection volume and the plane of the collection volume (collection electrodes) and the direction of the field is substantially perpendicular to the path of the radiation admitted into the detection volume. The electric field causes charge carriers between the first electrode and the collection electrode to drift toward the collection electrode at a substantially constant drift velocity. The chamber itself, including the detection and collection volumes, is mechanically coupled to apparatus which moves the chamber in a direction opposite to the direction of drift of the charges at a constant velocity of a magnitude substantially equal to the magnitude of the drift velocity of the charges. The currents flowing in the plural collection electrodes resulting from charges produced on the collection electrodes by the charge carriers is sensed. The spatial distribution in two dimensions of the radiation admitted into the chamber is determined in response to the amplitude with respect to time of the sensed current flowing in the respective plural collection electrodes. The spatial distribution of radiation in the transverse direction is determined by the spacing of the collection electrodes. Thus, in a KCD system, two-dimensional information can be obtained using a one-dimensional array of collector electrodes.

Since the motion of the chamber is at the same velocity but in a direction opposite to the drift of the charge carriers created in the medium in the detection volume, the x-ray radiation passing through each small area of the patient in the x-ray beam is integrated over the time that it takes for the charge carriers in the detection volume to drift through the space of the volume. This integration, which is required in order to obtain adequate signal levels, was achieved in prior art fan-beam systems using two-dimensional arrays of collector electrodes comprised, by way of example, of 80 to 100 elements in the scan direction and 2000 elements in the transverse direction. The KCD system provides the same information using a one-dimensional detector array and thus avoids the cost and complexity of large two-dimensional detector arrays as in the prior art.

Within the detection volume, a grid separates the space between the first electrode and the collector volume into a drift region and a collection region. The grid shields the collector electrodes from any induced current caused by the charges in the drift region so that only ions in the collection region are detected by the collection electrodes. The spacing between the grid and collection electrodes is one factor effecting the resolution of the system. The data obtained at the collection electrodes is digitally processed to generate an image. In that sense, KCD is a form of digital radiography.

Digital radiography is a general term encompassing a broad spectrum of activities within diagnostic medical imaging. In an early form, radiographic films were digitized in an attempt to enhance and redisplay information of interest. The field has evolved to its current state in which x-ray signals are detected electronically, converted to digital form, and processed prior to being recorded and displayed. In some cases, film is used for archival storage while in other implementations it is totally excluded from the process.

A primary goal of digital radiography is the removal of interfering effects from uninteresting structures in an image so that clinically significant details can be displayed with enhanced visibility. This process can simplify and extend the accuracy of diagnostic procedures. Two types of subtraction techniques have been developed to accomplish this goal: temporal or mask mode subtraction, and energy or spectral subtraction. Temporal subtraction is used primarily in angiography, while energy subtraction has applications both in angiography and general radiography.

In temporal subtraction, images are typically acquired before and after intravenous injection of an iodinated contrast medium. These images are then subtracted and enhanced in a digital processor to yield an image of arteries that is devoid of shadows due to bone and surrounding soft tissue. If the patient moves between the time that the mask and contrast images are obtained, artifacts are introduced into the subtracted image, possibly interfering with the diagnostic utility of the study.

Energy subtraction is based on the fact that x-ray attenuation is an energy-dependent phenomenon and, moreover, that the energy dependence is different for materials having different average atomic numbers. In energy subtraction, images are acquired using different x-ray spectra, digitized, and combined in a digital processor to selectively suppress signals due to some material or enhance signals due to others. This technique can be used to image either administered or inherent contrast differences. In dual-energy imaging, x-ray attenuation data are obtained using two different x-ray beam spectra. These data can be combined in a variety of ways, each of which produces an energy subtracted image in which signals from a material of a specific atomic number have been eliminated. This process is therefore referred to as material selective imaging. In general radiographic applications it is useful for removing unwanted objects from an image. By way of example, bone shadows can be suppressed when lung nodules are being studied in chest radiography. When the images at the different x-ray spectra are acquired close together in time, this method is relatively insensitive to patient motion. There are, however, other limitations, such as residual bone shadows in tissue-cancelled images, that can interfere with the visualization of iodinated arteries in vascular imaging applications.

In general radiography, it is desirable to eliminate shadows or images due to competing anatomy. If the area of interest is lung tissue, for example, the image shadows due to intermediate bone structures may obscure the image of the tissue. When single energy imaging is performed, it is extremely difficult to separate an image of a specific material. However, dual energy imaging permits cancellation or separation of image signals created by specific materials.

Figure 1:
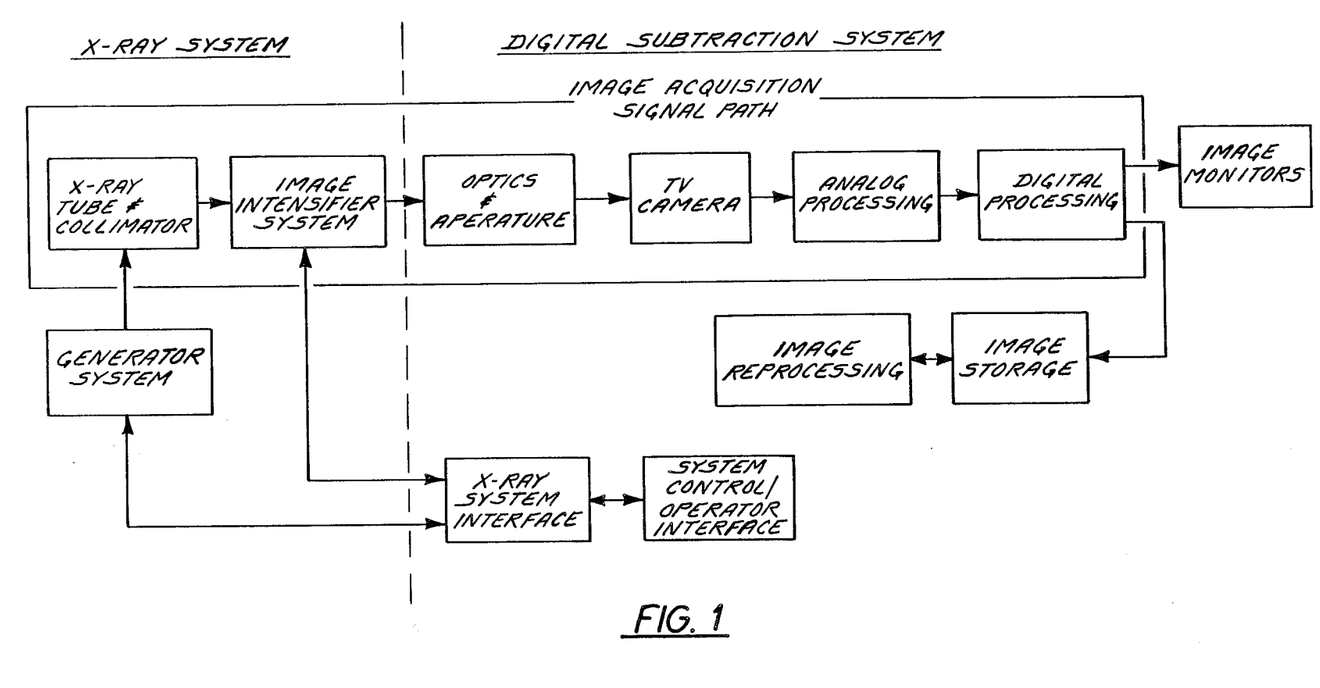
FIG. 1 is a functional block diagram of a basic digital fluorography system.

Before describing the present invention, a prior art system for performing both temporal and dual energy imaging will first be described along with the characteristics of such a system. FIG. 1 illustrates the basic functional components of a digital fluorography (DF) system which is used primarily for vascular imaging applications. The image acquisition signal chain utilizes a standard x-ray system generator, x-ray tube and image intensifier systems. The DF portion of the system starts at the output of the image intensifier where the image is optically coupled to a TV camera. Both analog and digital processing of the video signal can be used to enhance the image prior to display and/or image storage.

The arithmetic manipulation of images is central to the concept of DF. The ability to integrate images to reduce noise, to subtract pre- and post-contrast images, to enhance contrast, and to reprocess must be provided. In addition, a system controller is required to interface with the operator as well as to keep track of the various activities within the system. The first alternative is to use a minicomputer for both the controlling and arithmetic functions. The second is to use a distributed processor architecture with separate arithmetic and controlling elements. The drawback of minicomputers is that they cannot handle the data rates involved in DF if image rates greater than a few per second are to be used. The data and computational tasks for image rates up to 30 images/sec. can be handled by special-purpose hardware. The systemcontrolling functions are easily handled by a microprocessor.

Once the processing architecture is defined, the number of memories, their matrix size, and the number of bits per pixel need to be chosen. It is sometimes useful to integrate several frames to form a lower noise image even though the effective exposure time is lengthened. Memory depth greater than the number of bits in the incoming digitized video is required to perform this. Although it is possible to implement temporal subtraction using a processor with a singleframe memory, it is advantageous to have two, full-size memories since this configuration allows frames to be integrated for both the pre- and post-contrast images without a compromise in spatial resolution or precision.

A reasonable computational subsystem thus consists of a processor, a controller, and a programmable special purpose arithmetic processor.

Misregistration between the mask and the image in which the arteries of interest are opacified is one of the principal limitations of temporal subtraction DF.

One means of addressing the misregistration issue is to allow formation of alternate difference images. After the data are acquired, a subtraction is formed retrospectively between the contrast-filled, live image and an alternate mask image-one which better represents the orientation of surrounding structures in the image of interest. This procedure of selecting an alternate mask after completion of the injection procedure is called remasking.

A second means for addressing misregistration artifacts is dual energy subtraction. In digital fluorography, an X-ray image intensifier tube is used to obtain the image and it is viewed with a video camera whose signals are digitized and stored as an image frame. After the relatively low energy image is obtained, another image is obtained with a comparatively higher voltage applied to the X-ray tube and a resulting higher average energy spectral band. For ordinary tissue studies the two images may be made in the absence of any contrast medium. For arteriographic studies, the two images are obtained when there is an X-ray contrast medium such as an iodinated compound present in the blood vessels.

In any case, the high average energy image picture element (pixel) data are subtracted from the low average image data and a difference image remains. Prior to subtraction, the data are usually variously weighted or scaled to bring about cancellation of soft tissue. The data could be scaled to reduce bone, too. However, it is not possible to remove or cancel bony structures without also removing most of the iodinated contrast medium which is really what one is trying to visualize in arteriographic studies.

There are also brightness non-uniformities in the subtracted or difference image due to several effects when the data are acquired using an image intensifier. Veiling glare, which is like haze, results from light diffusing or feeding back from areas of the input fluorescent screen of the intensifier to other areas. The fact that rays of a broad X-ray beam are scattered by body tissue in an energy dependent manner between ray paths also causes loss of image contrast. Differential detection of X-rays at various energies in the input phosphor of the image intensifier leads to additional brightness non-uniformities. None of these phenomena can be completely nullified by energy subtraction alone.

A third technique for eliminating motion artifacts in a DF is the hybrid subtraction method described by W. R. Brody in U.S. Pat. No. 4,445,226 with implementation alternatives described by G. S. Keyes et al. in U.S. Pat. No. 4,482,918. The hybrid subtraction method uses a combination of energy and temporal subtraction techniques. In hybrid subtraction, X-ray images are obtained at two different average X-ray energies, that is, with two different kilovoltages applied to the tube and the images are combined in a manner to suppress signals due to soft tissue in a heterogeneous object such as the body.

At this juncture it should be noted that the X-ray beams having low and high average energies or energy spectral bands can be obtained in various ways. One way is by applying a constant kilovoltage (kV) to the X-ray tube and interposing two different filters alternatingly in the beam. One filter is for softening the X-ray beam, that is, for removing high energy spectra above a low energy average energy band. Typically, a desired low energy spectral band is determined and a filter is chosen that has relatively low attenuation at X-ray energies below its k-edge and has high attenuation for energies above the k-edge to thereby remove such high energy spectra. A filter made of a rare earth element such as cerium or erbium are examples. The other filter is for hardening the high energy beam and would be composed of a material that attenuates or absorbs the low energy band intensely. Thus, the high energy spectra filter can be aluminum, copper or brass, as examples.

Another way to generate low and high average energy X-ray beams is to switch the X-ray tube applied voltages between low and high levels. Still another way is to switch the X-ray tube applied voltage and switch filters correspondingly. This is the preferred way.

In hybrid subtraction a mask image is obtained first by projecting a low average energy X-ray beam (hereafter called low energy beam or low energy spectral band) through the body followed by a higher average energy X-ray beam (hereafter called high energy beam or high energy spectral band) when the intravenously injected X-ray contrast medium has not yet entered the blood vessels in the anatomical region of interest. The images, consisting primarily of bone and soft tissue acquired at the two energies, are scaled or weighted, using appropriate constants, and then subtracted to produce a mask image in which signals due to soft tissue variations are suppressed and bony structures remain. The data for a pair of high and low energy X-ray images are next obtained when the intravenously injected iodinated compound or other X-ray contrast medium reaches the vessels in the region of interest. The data for this pair of images are acted upon by the same constant weighting factors that were used with the first pair of images and one image in this pair is subtracted from the other such that the resulting post-contrast image contains data representative of bone structures plus vessels containing contrast medium. The final step in hybrid subtraction is to subtract the dual energy post-contrast image from the dual energy pre-contrast mask image to thereby suppress or cancel the bone structures and isolate the contrast medium containing vessels. A major advantage of the hybrid subtraction technique over temporal subtraction alone is the reduced sensitivity to soft tissue motion artifacts because the soft tissue is suppressed or cancelled in both dual energy images.

Hybrid subtraction is a good technique for eliminating anything that may have moved during the time between obtaining the mask image and post-contrast image or images. However, if there is no movement during ordinary temporal subtraction, wherein the post-contrast image is simply subtracted from the precontrast mask image, then temporal subtraction images can be used because they generally have a better signal-to-noise ratio (SNR) than hybrid subtraction images. A higher SNR results in displayed images that have better contrast at a given noise level.

Scattering of the X-ray beam by the body is also considered. Scatter in an image depends on X-ray beam energy, beam path length and density of the object being penetrated. In the hybrid subtraction technique the scattering that results from use of a broad cross section X-ray beam is of little consequence since scatter is essentially the same for each energy subtracted pair of images. Hence, scatter effects on image brightness non-uniformities are subtracted out when the pairs are subtracted.

To recapitulate, hybrid digital fluorography techniques provide the merits of soft tissue motion insensitivity, effective bone cancellation, and elimination, to the first order, of scatter and other nonlinear effects in the X-ray image intensifier and the video camera.

The prior discussion has dealt with one type of dual-energy imaging system which is particularly useful for vascular imaging protocols. Limitations to this dual energy approach imposed by X-ray scatter, veiling glare, and other nonlinear energy dependent effects in the imaging chain have been pointed out. An improvement, namely hybrid subtraction, has been described which deals with the limitations in vascular applications where administered contrast is being imaged. However, in general radiography alternative implementation for dual energy subtraction must be used because inherent contrast differences between relatively static anatomical components are being imaged. The major differences are in the apparatus used for the detection of the low and high energy X-ray images. Once these dual energy image pairs have been acquired and converted into digital data, techniques and apparatus described above and well-known to those schooled in the art can be used to process, display, and archive the dual energy subtracted images.

In a general radiography system, a dual energy image can be obtained by exposing a patient to two time-spaced energy beams, one at a low average energy and one at a high average energy. The two beams can be obtained by changing the anode-to-cathode voltage on an x-ray tube, by using two x-ray tubes or by inserting filters into the x-ray beam to change its average energy. Another technique which has been investigated is the use of two aligned detectors separated by a beam filter. The first detector may be a low atomic number detector while the second is a high atomic number detector. A discussion of dual energy imaging is given in Volume 156, No. 2, pages 537–540, of *Radiology* journal in an article entitled "Detector for DualEnergy Digital Radiography" by Barnes et al.

As will be apparent from the foregoing discussion, dual energy difference imaging, while required in order to provide a clinically useful image in many instances, has been subject to numerous implementation problems. A further example of implementation difficulties was experienced in attempts to develop a dual energy projection imaging device using a computerized tomography (CT) system with switched energy bands. In that system, X-ray energy was switched at a frequency sufficient to generate a pair of interlaced images, i.e., adjacent scan lines of a standard image format were obtained at a high and a low average energy. Although this arrangement was successful in eliminated motion artifacts, it gave up some resolution since only half of the scan lines were available for each image. It might also be noted that the scan lines were adjacent rather than overlapping and therefore not at exactly the same image point. However, they were sufficiently close so as not to significantly effect imaging results.

Since the KCD system is a scanning imaging device, difficulties arise if the low energy and high energy images are obtained serially, i.e., the object is scanned first with a low average energy x-ray beam and then scanned with a high average energy x-ray beam. The time between imaging a given point in the object with the low and high average energy beams would necessarily be at least as long as the time for a single detector to scan the field of view of the KCD system. Such a long time span between the imaging of a point with the two beams is undesirable because of patient motion and image registration problems.

As explained above, the KCD system accumulates charges during the time which the detection volume passes by a point in the target. Therefore, if an interlaced scheme, i.e., a detector forms the low energy image of a portion of the object while the x-ray beam energy is set low and then forms the high energy image of another portion of the object when the beam energy is high, of dual energy imaging is used, there must be a delay between the termination of the x-ray beam pulse of one energy and the start of the x-ray beam pulse of the other energy. If this delay is less than the time it takes for an ion to drift the length of the collection volume, part of the signal from the detector will be due to both the low energy and high energy x-ray beams. However, if a delay is used such that the signal from the detector is not a mixture of signals from the high and the low energy pulses, more than two separate detection volumes must be used in order to obtain a uniform patient exposure for each of the x-ray beams.

SUMMARY

In accordance with one object of the present invention and in one form thereof, dual energy difference imaging is obtained in a KCD system using two Kinestatic Charge Detectors located on the circumference of a circle that has its center at the focal spot of an x-ray source. The two detectors are separated a predetermined distance and move about the circumference of the circle at a constant velocity. The gas pressures and electric fields of each detector are adjusted so that the ion drift velocity in each detector is equal in magnitude but opposite in direction to the motion velocity of the detectors. Radiation from the x-ray source is directed toward the detectors and controlled whereby radiation of a first average energy is admitted to the first detector and radiation at a second average energy is admitted to the second detector. The data from one detector forms a low energy image while the data from the other detector forms a high energy image. A data processing system aligns the two images and creates a difference image. In one form the radiation energy is controlled by using filters positioned between the x-ray source and each detector. In another form, the x-ray source is switched between high and low energy states and a synchronized slotted apparatus is used to direct low energy radiation at one detector and high energy at the other. In a third form, low energy and high energy x-ray detection volumes are aligned along a single beam from a constant x-ray energy source.

DESCRIPTION OF THE DRAWING

For a better understanding of the present invention, reference may be had to the following detailed description taken in conjunction with the accompanying drawing in which.

DESCRIPTION OF THE PREFERRED EMBODIMENT

Figure 2:
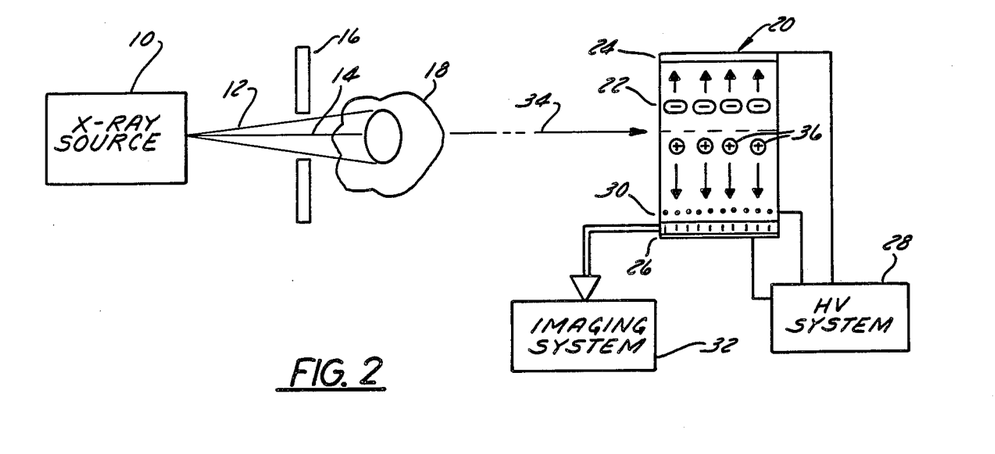
FIG. 2 is a simplified illustration of a kinestatic charge detector system.

FIG. 2 is a simplified illustration of a kinestatic charge detector (KCD) system of a type with which the present invention is particularly useful. A detailed description of a kinestatic charge detection system can be had by reference to the article entitled "Kinestatic Charge Detection" by Frank A DiBianca and Marion D. Barker, published in the May/June, 1985 edition of *Medical Physics*, vol. 12, #3, pp. 339–343, and in pending patent application Ser. No. 721,727 filed Apr. 10, 1985 for DiBianca. In this system, an x-ray source 10 provides a beam of x-ray radiation 12 which is collimated by passage through a slit 14 in a collimator 16. The x-ray beam is typically 8 to 10 mm wide in the plane of FIG. 2 and 350 to 500 mm wide perpendicular to the plane of FIG. 2 at the entrance of the detector. These two directions are referred to as the scan direction and transverse direction, respectively. The x-ray radiation passes through a patient 18 and the attenuated radiation then enters into an ionization chamber 20 of the kinestatic charge detection system. For purposes of discussion, the KCD system may be but is not limited to use of a gas-filled ionization chamber. The chamber 20 includes an ionization space 22 preferably containing a heavy gas such as xenon in a region between a planar anode 24 and a parallel planar collector electrode 26. A voltage source 28 is connected between the anode 24 and the collector electrode 26 to induce an electric field across the space 22 in the region between the two electrodes. A parallel planar grid 30 is also located in the space 22 adjacent the collector electrode 26. The grid 30 is also provided with an electrical potential from the high voltage source 28.

An x-ray photon which is absorbed in the gas within the space 22 typically produces a photo electron which in turn produces a number of electron/ion pairs in the gas. Electrons drift rapidly to the anode 24 while the ions drift much more slowly to the cathode or collector electrode 26. Because a relatively large voltage is present on the grid, the ions accelerate through the grid and reach the collector electrode 26. The number of ions which reach the collector electrode 26 can be controlled by adjusting the voltage of source 28 so that the electric field between the grid and the collector electrode is sufficient to assure that a continuous field is present to direct the ions toward the collector electrode. An imaging system 32 receives signals from collector electrode 26 representative of the quantity and distribution of ions reaching the electrode. The imaging system 32 uses this data to construct an x-ray image of the patient 18. The imaging system 32 includes a data acquisition system, a computer, processing electronics, electronic data storage and image presentation equipment, all of a type known in the art for reproducing images from digital data.

Chamber 20 is physically moved with respect to a radiation path 34 at a velocity $V_{scan}$ having a magnitude equal to that of the velocity $v_{drift}$ at which the charge carriers 36 in chamber 20 are drifting. The direction in which chamber 20 is moved is opposite to the direction in which carriers 36 are drifting (and is thus perpendicular to the direction of path 34 of the incoming x-ray beam) and has the effect of making the drifting charges stationary with respect to path 34. The charge carriers drift with respect to the chamber 20 at a constant velocity, and chamber 20 is synchronously moved in a manner exactly opposite to the manner in which the charge carriers drift. Therefore, the charge carriers remain stationary with respect to path 34 for as long as the path intersects detection volume or space 22. All x-ray photons traveling along path 34 contribute to charges in proximity to the path. Similar integration occurs with respect to every other path drawn through the patient 18 while the KCD sweeps past that path.

The apparatus and control system for moving the chamber 20 are not considered part of the present invention. Such apparatus may comprise a mechanical structure to which the chamber 20 and associated equipment are mounted. Servo drive systems may be provided to move the chamber 20 about an arc of a circle at a predetermined velocity by means well known in the art. Both the chamber 20 and collimator 16 are rotated such that the x-ray radiation scans across the patient 18 who remains stationary.

Figure 3:
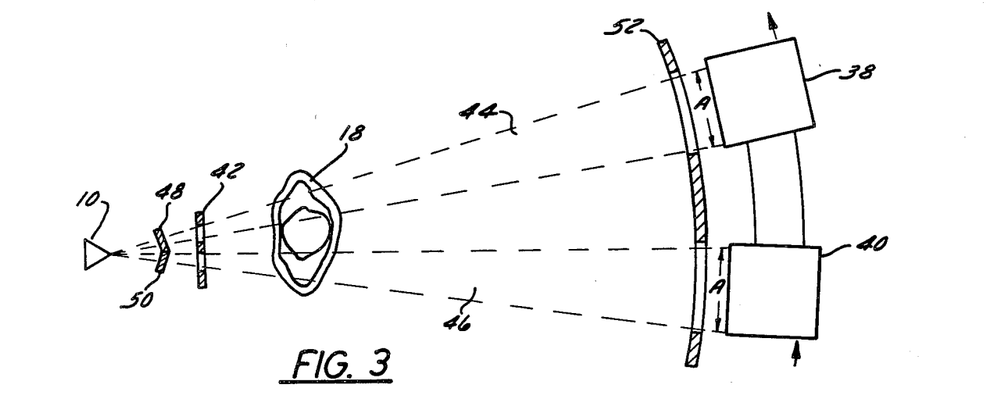
FIG. 3 is one embodiment of the present invention using first and second Kinestatic Charge Detectors for obtaining a dual energy image.

Turning now to FIG. 3, there is shown a first embodiment of the present invention using first and second Kinestatic Charge Detectors 38 and 40. For purposes of explanation, detector 38 will be assumed responsive to x-ray radiation at a relatively low average energy and detector 40 will receive x-ray radiation at a relatively high average energy. A collimator 42 forms the x-ray radiation into two fan beams 44 and 46. Collimator 42 comprises a radiation impervious sheet having a pair of slits or slots for passing the fan beams 44 and 46 and is shown in crosssection.

Before reaching the collimator 42, the beams 44 and 46 pass through respective filters 48 and 50. The anode-to-cathode voltage of x-ray tube source 10 is maintained at a constant value so that the average beam energy remains constant. The filters 48 and 50 are of a type well known in the art and are selected such that the average energy of the x-ray radiation in beam 44 is less than the average energy of the x-ray radiation in beam 46. A second collimator 52 is provided in the region of the detectors 38 and 40 for preventing or at least minimizing the scatter effect, i.e., preventing x-ray radiation scattered from beam 46 from reaching detector 38 and radiation from beam 44 reaching detector 40.

As the apparatus effects rotation of the detectors 38 and 40, along with synchronized rotation of collimators 42 and 52 and filters 48 and 50, the fan beams 44 and 46 scan across the patient 18. The detector 38 produces data for forming the low energy image and detector 40 produces data for forming the high energy image. The data from each detector 38 and 40 are processed by the imaging system 32 to yield a dual energy difference image. The general processing techniques are well known in the x-ray art.

Figure 4:
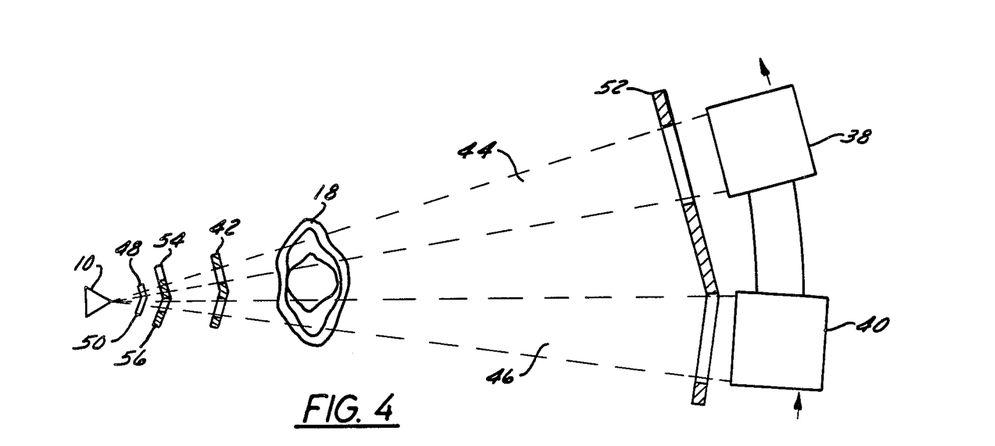
FIG. 4 is another embodiment of the present invention for dual energy imaging using a KCD system.

For purposes of simplifying the drawings, the patient or target 18 is shown as being near the x-ray source 10 and spaced from the KCD chambers 38 and 40. In an actual system, the patient 18 will be much closer to the chambers 38 and 40 and spaced from the x-ray source 10. The collimators, shutters and filters will be similarly repositioned while maintaining their respective locations with respect to each other. The system as shown in FIGS. 3 and 4 allows visualization of component placement without distortion. More particularly, the beam width A at the entrance to KCD chambers 38 and 40 is typically between 2 and 10 millimeters. If drawn to scale, the target 18 would completely cover and obscure all other portions of the system.

The widths of the fan beams 44 and 46 can be chosen to optimize the signal-to-noise ratio (SNR) and patient x-ray exposure or dosage. Fan beam width is adjusted by changing the width of the slots in collimator 42. It should also be noted that the spacing between the detectors 38 and 40 should be maintained at a minimum value so as to minimize the time between data acquisition in each detector. As the time between images increases, the likelihood of introducing motion artifacts due to patient movement also increases.

An advantage of the system of FIG. 3 is its simplicity. The x-ray source voltage is maintained at a constant value thus avoiding high-voltage switching problems and synchronizing of switching with detector motion. However, separation of the energy spectrum of each beam using filters is limiting. Although the two beams have different average energies, each beam includes energy of a wide range. Thus, there tends to be an overlap of energy spectra between the beams. Such energy overlap reduces the ability of the difference technique to subtract out artifacts or competing images.

An alternate embodiment of the present invention for dual energy images in a KCD system is shown in FIG. 4. In this embodiment, the anode-to-cathode voltage of x-ray source 10 is varied between two different values at a predetermined frequency. A pair of shutters 54 and 56 are each shifted in-and-out of the respective fan beams 44 and 46 at the frequency at which the anode-to-cathode voltage is switched. Shutter 54 blocks the beam 44 when the voltage is at a high value while shutter 56 blocks the beam 46 when the voltage is at a low value. The shutters 54 and 56 are x-ray impervious and their mechanical construction well known in the art. The shutters may be electromechanically controlled by means well known in the art. One advantage of shutters is the independent control of each beam exposure time. In this manner, only low energy radiation is admitted to detector 38 and only high energy is admitted to detector 40. If the ratio of the amount of time that the energy is high to the time that it is low is constant, the shutters 54 and 56 could be slots in a spinning disc. However, it is preferable to be able to vary the ratio in order to optimize the signal-to-noise ratio and patient dose. Further improvement may be realized by providing beam filters of different materials in each beam to provide more complete separation of the high and low energy spectra.

In order to reduce "banding" in the images, the frequency of switching and the times for which the energy is high and low must be selected such that every pixel in an image is exposed for the same amount of time. This will be true if:

$$F = N(V_{scan}/W_L),$$

$$N = 1, 2, 3 \ldots$$

and $$F = K(V_{scan}/W_H), \quad K = 1, 2, 3, \ldots$$

Where $W_L$ is the width of the fan beam 44 at detector 38, $W_H$ is the width of fan beam 46 at detector 40, and F is the frequency at which the x-ray energy is switched.

Figure 5:
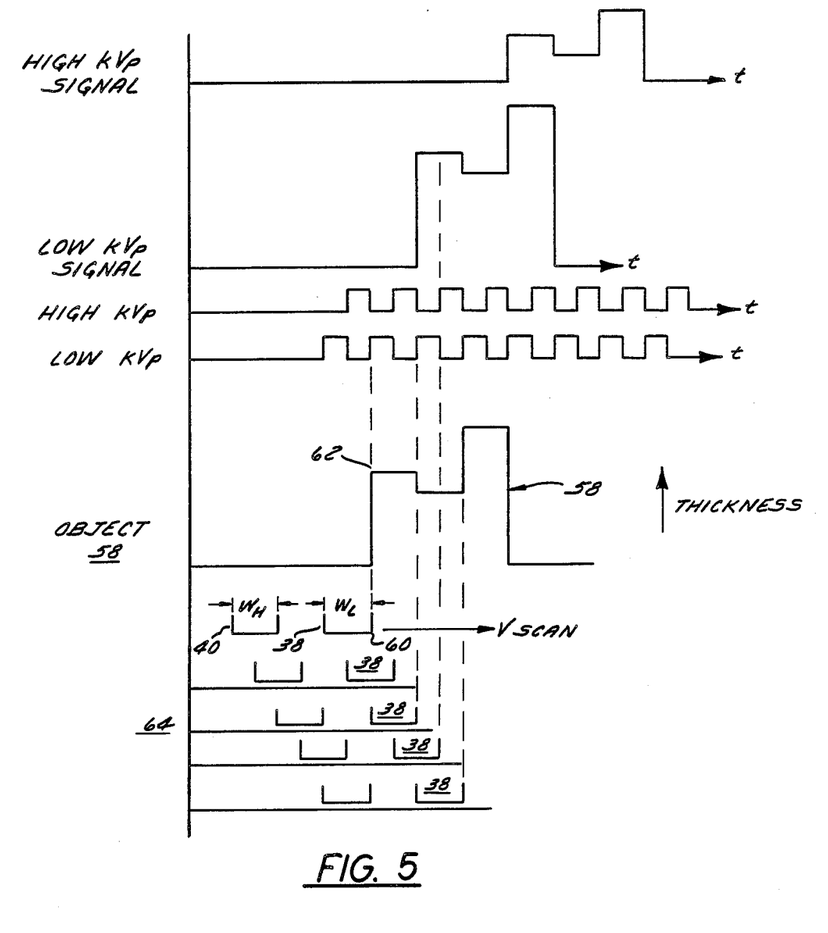
FIG. 5 is a timing diagram illustrating high energy and low energy x-ray intensities and scan results for a system such as FIG. 4.

A timing diagram is shown in FIG. 5 illustrating high energy and low energy x-ray intensities and scan results for a system in which the exposure frequency and beam widths are chosen such that $K = N = 1$. An object 58 is stationary while detectors 38 and 40 scan past. As the leading edge 60 of detector 38 intersects the leading edge 62 of object 58, the average x-ray energy is set at its low value as shown by the line labeled "Low kVp". When one-half of the width of detector 38 has passed behind object 58, the x-ray source 10 is switched to a higher average energy and the beam 44 is blocked. Detector 38 will therefore not detect any radiation while the average x-ray energy is high. The line labeled "High kVp" illustrates the high energy output times. When detector 38 has moved a distance equal to its width, the source 10 will switch back to its low kVp state and detector 38 will again be exposed to radiation. The position of detector 38 at the start of the second exposure is shown on line 64. The detector 38 again moves through a distance equal to one-half its width while admitting x-ray radiation.

The output signal developed by detector 38 is shown as "Low kVp Signal" and is delayed by the width of detector 38, i.e., the time that it takes detector 38 to move a distance equal to its width. The "High kVp Signal" developed by detector 40 is obtained in the same manner as the signal from detector 38 but follows by a time delay equal to the transition time for the spacing between detectors 38 and 40 and the width of the detectors. The relative amplitude of the signals developed by the two detectors is indicative of the intensity of the radiation admitted.

As can be seen, by switching between high and low average energy radiation in accordance with the timing diagrams of FIG. 5, each element of the object is exposed to both high and low average energy radiation and the radiation through each element is detected by a corresponding one of the detectors 38 and 40. Accordingly, two separate images are formed very closely in time at two different average energies. By controlling the spacing between the two detectors and the scan rate (and ion motion rate), the temporal spacing between images can be adjusted to minimize effects of patient motion. The frequency of switching, however, should be chosen high enough that every pixel in an image results from ions created at a large range of distances from the collector electrode 26. The effects of electric field non-uniformities, scattering, recombination, space charge and diffusion of the ion cloud, all of which are related to the distance from the collector electrode 26 at which ions are created, can be reduced if both K and N, i.e., the switching frequencies, are greater than two.

Figure 6:
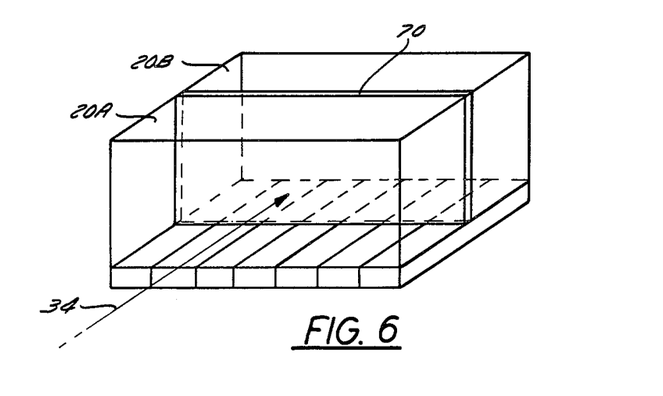
FIG. 6 is a representation of a KCD chamber formed as two independent front/back chambers separated by a radiation filter for obtaining dual energy images.

Another embodiment of the present invention for obtaining a dual energy image may be obtained by mounting the detectors 38 and 40 in alignment with a single fan beam rather than spaced to receive two different fan beams. A filter placed between the two detectors could remove the lower average energy component of the beam so that the second detector would detect images created by the higher average energy component. The detectors 38 and 40 could also utilize different atomic number x-ray detection media. A further refinement is to construct a single front/back split KCD chamber. As with the aligned dual chambers, this refined system would only require a single average energy beam. FIG. 6 is a representation of a KCD chamber 20 formed as two independent chambers 20A and 20B separated by radiation filter 70. The filter 70 is selected to establish an average energy in the beam reaching detector section 20B at a higher value than that detected in section 20A. The filter 70 may have a K-edge at 69.5 keV, for example. Beam 34 enters detector 20 as shown in FIG. 2. The two chambers may be two parts of a single KCD chamber separated by filter 70 or may be two isolated chambers operating with different gases (ion sources) at different pressures. The gases and pressures could optimally be selected to pass higher energy x-rays to the second or back chamber while allowing lower energy x-rays to interact with the gas in the first or front chamber. A lower atomic number gas, e.g., Krypton, could be used in the first chamber at a lower pressure than Xenon gas in the second chamber.

While the invention has been described in detail in accord with what is considered to be a preferred embodiment, many modifications and changes may be effected by those skilled in the art. Accordingly, it is intended by the appended claims to cover all such modifications and changes which fall within the true spirit and scope of the invention.

What is claimed is:

1. A kinestatic charge detection system comprising:
  a source of ionizing radiation;
  first and second kinestaic charge detectors each having respectively a chamber wherein each chamber includes a window for admitting ionizing radiation from said radiation source, a medium in each chamber ionizble by said radiation, electrically energized electrodes within each chamber for causing one of positive an negative ions generated in each chamber by the radiation to drift toward a corresponding electrode at a predetermined velocity;
  chamber moving means coupled to each chamber for moving each chamber in a direction opposite to the direction of drift of the ions in the chamber and at a velocity substantially equal thereto, said second chamber being mechanically coupled to follow said first chambrr through said radiation;
  collimator means positioned between said radiation and said detectors for collimating the ionizing radiation into at least a first and a second beam;
  means for establishing a first relatively low average energy level for radiation in said first beam and a said second relatively high average energy level for radiation in said second beam, said establishing means comprising:
    (i) means for switching the average radiation energy output of said radiation source between first and second valucs at a predetermined frequency; and
    (ii) means for alternately blocking said first and second beams for causing radiation of a first average energy level to impinge on said first chamber and radiation of a second average energy level to impinge on said second level;

means for directing said first beam onto said first chamber and said second beam onto said second chamber for forming a low energy image and a high energy image of a patient interposed in said radiation beams; and means for forming a dual energy difference image from the low and high energy images.

2. The system of claim 1 wherein said blocking means comprises a radiation impervious disc having at least one aperture radially positioned therein, said disc being positioned between the radiation source and the patient and beig rotated at a frquency sich that radiation at said first average energy value passes through sadi aperture to said first chamber and radiation at said second average energy value passes through said aperture to said second chamber.

3. The system of claim 1 wherein said blocking means comprised electromechanically actuated shutters synchronized with switchng of the radiation source.

4. The kinestatic charge detection system of claim 1 and including a forst filter positioned between said collimator means and the radiation source in alignment with said first beam, said filter establishing an average energy in said first beam at a value different than an average energy in the second beam.

5. The system of claim 4 and including a second filter positioned between said collimator means and the radiation source in alignment with said second beam, sadi second filter establishing an average energy of said second beam different from the average energy of said first beam.

* * * * *